(12) United States Patent
Lamotte

(10) Patent No.: US 7,749,776 B2
(45) Date of Patent: Jul. 6, 2010

(54) LIQUID FLOW ASSAYS UTILISING A COMBINED DETECTION AND CONTROL ZONE

(75) Inventor: Richard Lamotte, Perthshire (GB)

(73) Assignee: Lateral Laboratories Limited, Perthshire (GB)

( * ) Notice: Subject to any disclaimer, the term of this patent is extended or adjusted under 35 U.S.C. 154(b) by 467 days.

(21) Appl. No.: 11/919,798

(22) PCT Filed: May 4, 2006

(86) PCT No.: PCT/GB2006/050091

§ 371 (c)(1),
(2), (4) Date: Nov. 16, 2007

(87) PCT Pub. No.: WO2006/117574

PCT Pub. Date: Nov. 9, 2006

(65) Prior Publication Data

US 2008/0310998 A1    Dec. 18, 2008

(30) Foreign Application Priority Data

May 4, 2005    (GB) ................................ 0508998.2

(51) Int. Cl.
*G01N 33/549*    (2006.01)
(52) U.S. Cl. .......................... 436/532; 422/56; 422/57; 422/58; 422/61; 436/501; 436/514; 436/518

(58) Field of Classification Search .................... 422/56, 422/57, 58, 61
See application file for complete search history.

(56) References Cited

U.S. PATENT DOCUMENTS

| 5,712,172 | A | 1/1998 | Huang et al. |
| 6,258,548 | B1 | 7/2001 | Buck |
| 2004/0241879 | A1 | 12/2004 | Robinson |

FOREIGN PATENT DOCUMENTS

| EP | 0 833 159 | 4/1998 |
| WO | 80/02076 | 10/1980 |
| WO | 00/31539 | 6/2000 |
| WO | 03/025573 | 3/2003 |

OTHER PUBLICATIONS

International Search Report issued Nov. 7, 2006 in the International (PCT) Application of which the present application is the U.S. National Stage.

*Primary Examiner*—Jill Warden
*Assistant Examiner*—Timothy G Kingan
(74) *Attorney, Agent, or Firm*—Wenderoth, Lind & Ponack, L.L.P.

(57) ABSTRACT

The invention relates to liquid flow assays widely applicable to target analytes, including haptens, which employ a detection zone which is a single combined analyte detection and control zone in a test strip or sheet and two labelled reagents with detectably distinguishable labels, preferably with visually contrasting colored particle labels, whereby both negative and positive samples are distinguishable by detection of different captured label signals in the detection zone.

14 Claims, 2 Drawing Sheets

LIQUID FLOW ASSAYS UTILISING A COMBINED DETECTION AND CONTROL ZONE

This application is a U.S. national stage of International Application No. PCT/GB2006/050091 filed May 4, 2006.

The present invention provides liquid flow assays for detecting an analyte in a liquid sample, which employ a combined detection and control zone in a test strip or sheet and two labelled reagents whereby negative and positive samples are distinguished by detection of different immobilised label signals. Such assays may take the format of a flow through assay in which liquid sample is applied to the combined detection and control zone in a porous test sheet and liquid flow is transverse to the plane of the test sheet or more preferably may take the form of lateral flow assays in which liquid sample permeates along a test strip or sheet comprising porous material. Preferably assays of the invention may take the form of lateral flow immunochromatographic assays.

BACKGROUND OF THE INVENTION

Liquid flow assays, either employing a flow through device or of the lateral flow type, are well known for detection of a variety of analytes in liquid samples including antigens such as hormones, e.g. human chorionic gonadotrophin (hCG) for pregnancy testing, antibodies such as antibodies to infectious agents and haptens such as drugs of abuse. Flow through devices have been described which provide for single label detection in different patterns depending upon whether a negative or positive sample is applied. Such devices are described for example in European Patent no. 0217403 of Abbott Laboratories. Most commonly, known lateral flow devices, however, provide a control zone for establishing correct use of the device which is distal from the analyte detection zone in the direction of liquid flow. By way of example reference may be made to European Patent no. 0291194 of Inverness Medical Switzerland GmbH and related European Patent nos. 0560410 and 0560411, and European Patent no. 0284232 of Becton Dickinson. Published European Patent Application no. 0833159 (Millipore) describes further such devices providing a capture zone presenting immobilised analyte or analyte analog for capture of analyte/antibody complexes, multiple readout zones for binding of biotinylated analyte also carrying detectable label and a control zone which binds a second labelled irrelevant analyte carrying a second distinguishable label. EP-B 0566695 of Quidel Corp. describes lateral flow devices also employing two detectably distinguishable labelled reagents in which a detection zone is provided including a distinct control portion for capture of labelled control reagent. Manufacture of all such assay devices requires separate careful application to the test strip or sheet of immobilised reagent to provide the control region.

U.S. Pat. No. 6,258,548 (Buck) teaches lateral flow assays which provide distinguishable visual signals in a single combined detection and control zone indicative of negative and positive assays. However, the assay concept described is solely applicable to large antigens having more than one epitope and for which a labelled portion can be provided which is distinguishable by antibody binding from the whole parent antigen. For example, the whole antigen may be hCG and the labelled antigen portion the alpha domain of hCG. In this case, anti-alpha hCG antibody is immobilised in the detection zone of the test strip or sheet.

Assays of the present invention utilise a combined detection and control zone but are applicable to all types of analyte including haptens. They can utilise either a sandwich assay or competitive assay format and may be applied to haptens and antigens, including antibodies. Furthermore, in one embodiment the detection/control zone employed is a universal detection zone. This means identical strips or sheets comprising porous material and containing the detection zone can be manufactured for use in multiple assays for different analytes. For use in lateral flow assays, such a test strip or sheet may be joined with different label release zones, which provide the required labelled reagents.

SUMMARY OF THE INVENTION

The present invention provides a liquid flow assay for detection of a target analyte in a liquid sample wherein the liquid sample flows through or along a test strip or sheet comprising a porous material and said test strip or sheet has a detection zone for said analyte wherein said analyte is detected by a specific binding assay of a sandwich or competitive format, characterised in that said detection zone is a single combined analyte detection and control zone wherein any target analyte is contacted with a first labelled reagent and a second labelled reagent provided as mobile reagents and carrying detectably distinguishable labels, at least one of said labelled reagents being a component for said specific binding assay and at least one of said labelled reagents becoming immobilised throughout the detection zone independently of the presence of target analyte through a specific binding reaction with an immobilised reagent which does not bind target analyte, whereby irrespective of whether the sample is a positive or negative sample a captured label signal is detectable in the detection zone, positive and negative samples being distinguishable by detection of different captured label signals. In this way, a separate control zone need not be provided. Such an assay is applicable to a variety of analytes, including DNAs, RNAs, oligonucleotides, aptomers, antibodies, antigens and haptens.

As indicated above, such an assay may employ a flow through device of conventional form. Alternatively, such an assay may be a lateral flow assay. Preferably the assay may be an immunoassay, most preferably an immunochromatographic assay employing two direct labels which can be visually distinguished.

Especially preferred our assays of the invention which employ a universal detection zone as mentioned above. In this embodiment, both the said first and second labelled reagents are components of the specific binding assay for the target analyte, one of the said labelled reagents additionally carrying a first member of a specific binding partner pair which binds to the second member of said pair immobilized in the detection zone. The said specific binding partner pair may be any specific binding partner pair which is irrelevant to target analyte binding. However, it may be preferred to employ a biotinylated labelled reagent in which case the detection zone will carry an immobilized specific binding protein for biotin such as avidin, streptavidin, neutravidin or anti-biotin antibody. It will be appreciated that the reagents for the specific binding assay can freely mix with any target analyte prior to capture of one or both labels in the detection zone and that such dynamic mixing of analyte and specific binding reagents enhances assay performance.

In an alternative embodiment, only one of the labelled reagents is involved in the specific binding assay for the target analyte. In this case, the detection zone will present immobilised capture reagent for said specific binding assay and, interdispersed therewith, a second immobilised reagent to bind the second labelled reagent (the control reagent) independently of the presence of target analyte. Such a combined analyte detection and control zone will be formed by coating a zone of a porous strip or sheet with a mixture of the two reagents to be immobilised whereby both reagents become immobilised throughout that zone. For such assays the control labelled reagent may be chosen so as to have substantially the same migration characteristics as the labelled reagent for analyte detection, Thus, for example, if labelled antibody is provided specific for target analyte, then a second labelled antibody which is irrelevant to target analyte binding may be desirably provided as the control reagent. However, alternatively a control reagent and immobilised specific binding partner for the control reagent may be provided such that the control signal develops slower than any test signal or such that the reagents for the analyte specific binding assay are presented first in the combined analyte detection/control zone.

Whichever embodiment of the invention is employed, a signal is detectable in the detection zone regardless of the sample being positive or negative. This is an important advantage in relation to conventional liquid flow assays employing a competitive assay format with which positive samples lead to reduction of signal or no signal.

In another aspect, the invention provides a kit for carrying out a liquid flow assay of the invention comprising (i) two labelled reagents carrying distinguishable labels as discussed above and (ii) a test strip or sheet comprising a porous material and providing a combined analyte detection/control zone as discussed above.

In a further aspect, the invention provides a test strip or sheet for performing a lateral flow assay of the invention which has the following features:

(i) a strip or sheet comprising a porous material, preferably nitrocellulose, which provides the required detection zone; and (ii) joined to, or integral to, said strip or sheet providing said detection zone, a label release zone which is capable of releasing into liquid drawn into that zone the required labelled reagents, e.g. two labelled antibody reagents carrying different coloured particle labels of visually contrasting colours.

Throughout this specification "labelled" will be understood to mean either directly labelled or indirectly labelled, e.g. by means of secondary labelled antibodies.

The above noted embodiments of the invention will now be described below in more detail with reference to the following figures:

Figure 1:
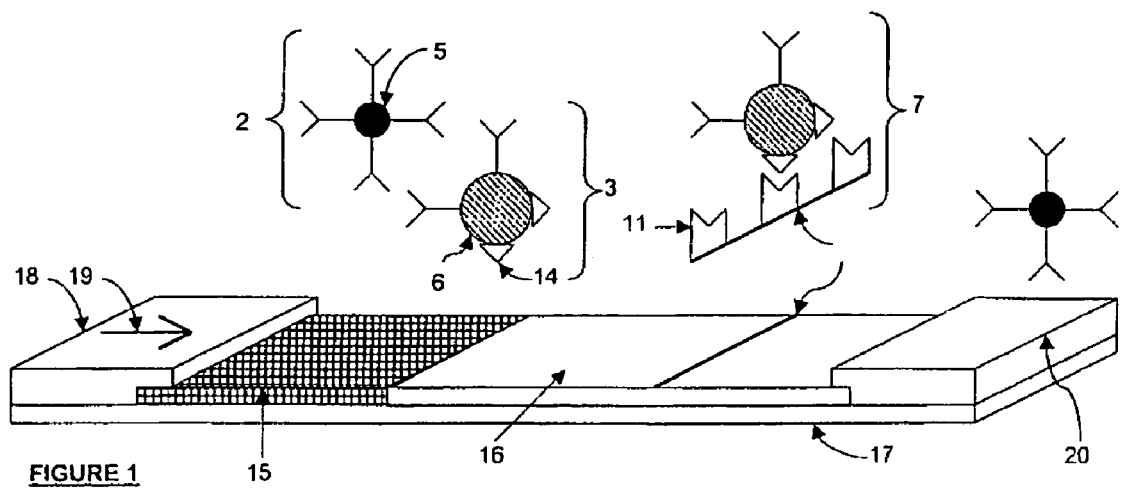
FIG. 1.
Figure 2:
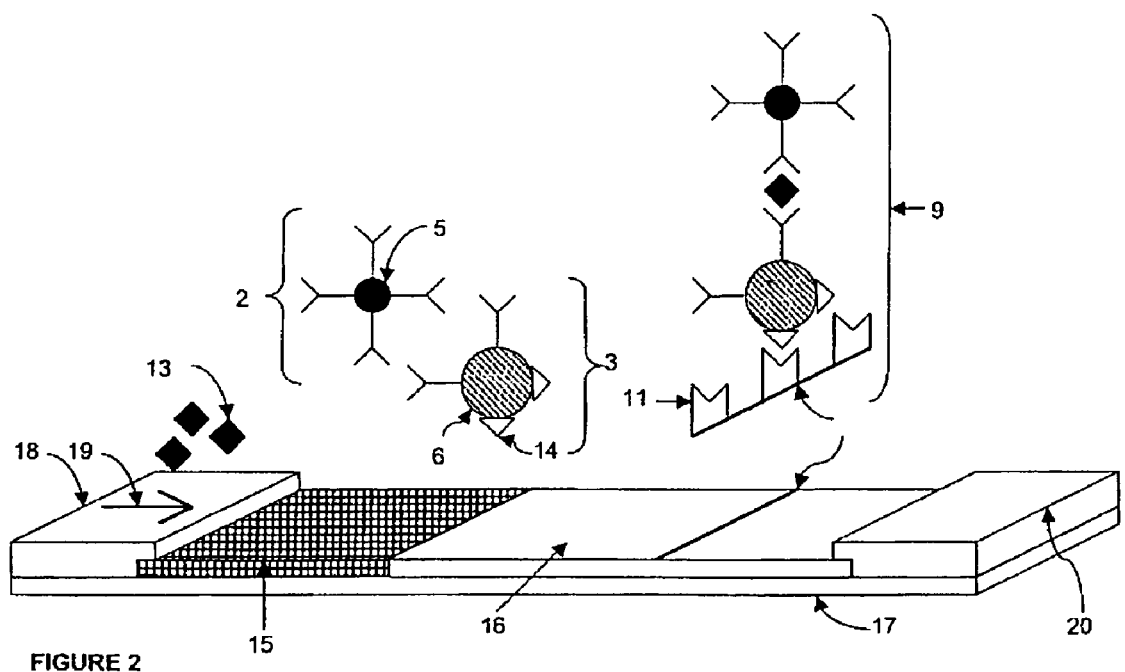
Figure 3:
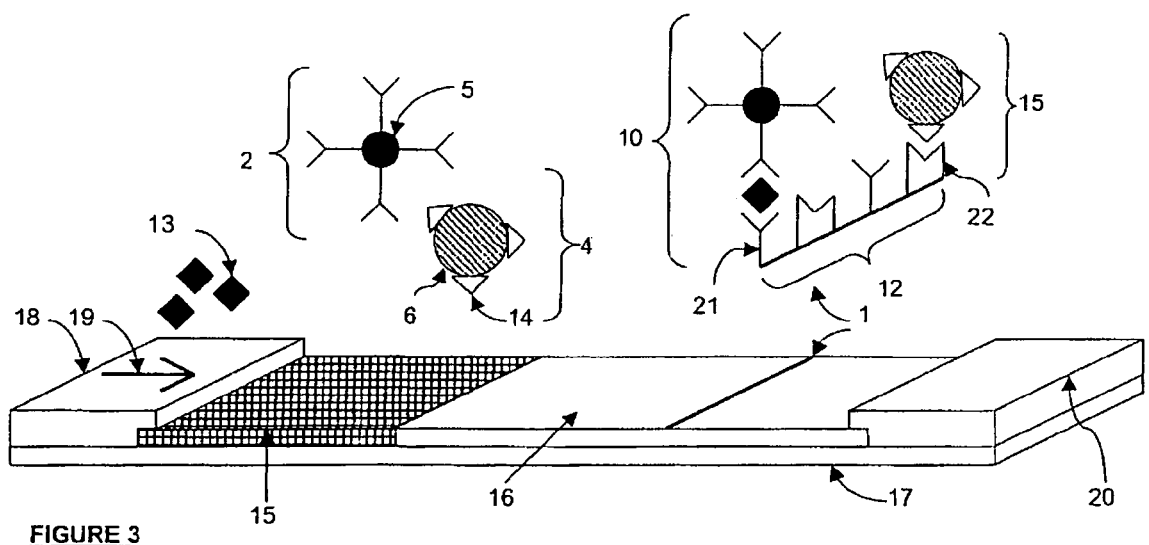

Illustrates the universal capture zone embodiment in the absence of target analyte. Only the labelled reagent which carries specific binding partner for the capture reagent immobilised in the universal capture zone becomes bound in that zone.

FIG. 2:

Illustrates the universal capture zone embodiment with detection of target analyte using two labelled reagents which are specific binding partners for that analyte. In the presence of target analyte, the labelled reagents form a complex with the analyte and as one of the labelled reagents additionally carries a specific binding partner for the immobilised reagent in the universal capture zone, the whole complex is bound in the detection zone and a combination of both of the label signals is seen.

FIG. 3:

Illustrates the mixed capture zone embodiment wherein one of the labelled reagents carries a specific binding partner for one of the reagents immobilised on the capture zone. The other labelled reagent and other immobilised reagent are specific binding partners for the target analyte, so it is only in the presence of target analyte that both labelled reagents will become bound in the capture zone.

DETAILED DESCRIPTION OF THE INVENTION

As indicated above, the essential features shared by liquid flow assays of the invention are wide applicability coupled with a combined analyte detection and control zone [1] and use of two labelled reagents [2, 3, 4] with detectably distinguishable labels [5, 6] whereby both positive and negative samples generate a signal in the same detection zone but the two signals are different. Desirably, the labels may be colour labels whereby, for example, a negative result corresponds with detection of a colour corresponding to a single captured colour label [7] and a positive result arises from detection of a combination of both colours [9, 10]. The combined analyte detection and control zone [1] may present a single immobilised reagent (a universal capture reagent) [11] or a mixture of two immobilised reagents throughout the zone [12]. Each of these embodiments will now be separately further described.

The Universal Capture Zone Embodiment

For assays of this embodiment, the two labelled reagents [2, 3] provided may be two specific binding partners for the target analyte [13], e.g. two labelled antibodies directed to different epitopes of the target analyte, suitable for carrying out a sandwich assay, or a labelled specific binding partner for the target analyte, e.g. a labelled antibody, and a labelled analyte or analyte analogue suitable for carrying out a competitive assay. One of the two labelled reagents will also carry one member of a specific binding partner pair [14], the second member of which is immobilised in the analyte detection zone of the test strip or sheet [11]. As indicated above, this specific binding partner pair may be any specific binding partner pair which is irrelevant to target analyte binding, e.g. two complementary oligonucleotides, an antibody/antigen binding pair, a lectin/lectin binding protein pair or a vitamin/vitamin binding protein pair. Preferably, biotin and a biotin binding protein (e.g. avidin, streptavidin, neutravidin or anti-biotin antibody) may be employed. Thus, as indicated above, conveniently one labelled reagent may be additionally biotinylated for binding to an immobilised specific binding protein for biotin such as avidin, streptavidin or neutravidin. It will be appreciated that in this way a combined analyte detection and control zone [11] is provided which may be used with any analyte.

Labels

The two labels [5, 6] employed must be detectably distinguishable. They may be selected from any of the conventional types of labels used in specific binding assays including enzyme labels, radioisotopes, fluorescent labels and chemiluminescent labels. Preferably, however, both labels will provide a direct visual signal, e.g. coloured particles such as coloured latex beads, collidal gold and dye labels or fluorescent labels. It is most preferred to employ labels which provide visually contrasting colours whereby immobilisation of both labels is indicated by a colour combination. It will be appreciated that one of the labels may be a far stronger colour than the other. In such a case, where both colour labels are captured, one colour of the combined colours may in fact dominate. Thus, for example, one labelled reagent may carry a gold label (detected alone as red colour) and one labelled reagent may carry green beads. In this case, immobilisation of both reagents in the combined analyte detection and control zone will be indicated by appearance of brown/red colour. Alternatively, for example, one labelled reagent may carry yellow latex beads and the other labelled reagent may carry blue latex beads. In this case, capture of both labelled reagents in the combined analyte detection and control zone will be indicated by appearance of green colour. By observing the precise colour of the detection zone with different concentrations of target analyte, qualitative, semi-quantitative or quantitative assays may be carried out with actual test samples.

Thus, for example, in the case of use of a sandwich assay format for detection of target analyte employing two contrasting colour labels (red colloidal gold and green latex beads), in the absence of target analyte the detection zone will appear red or green depending upon which colour-labelled specific binding reagent for the target analyte additionally carries the binding partner for the capture reagent immobilised in the detection zone of the test strip or sheet. With presence of target analyte, the detection zone will change to brown/red colour. The precise colour will depend on the ratio of the two labels immobilised in the detection zone which in turn is dependent on the amount of target analyte in the sample. Thus, such an assay may be designed such that weak positives are indicated by detection of brown/red and strong positives by detection of red as red is the dominant colour. Such an assay is described in more detail in Example 1. Since in such an assay visual signals from both of the labelled reagents are being observed with a positive sample, there is amplification of positive signal compared to a conventional liquid flow assay employing a single labelled reagent.

In the case of use of a competitive assay format employing two contrasting colour labels, in the absence of target analyte, the colour observed in the detection zone will represent the combined colour of the labels, e.g. brown/red if the labels are collidal gold and green latex beads, or green if blue and yellow latex beads are employed. In the presence of target analyte, there will be reduction in immobilisation of one colour label due to reduction in complexing of colour-labelled specific binding reagent to colour labelled analyte or analyte analogue. Hence, the colour of the detection zone will be observed to change. Such an immunoassay employing biotinylated analyte labelled with coloured latex beads and antibody for the analyte labelled with a second colour label is described in Example 2. It will be appreciated that an equivalent assay may be carried out in which the antibody is biotinylated rather than analyte. In this case, the colour of the detection zone will change to the colour of the antibody label with increasing analyte in the sample.

Lateral Flow Assays

As indicated above, assays of the invention employing a universal detection zone [11] as discussed above may preferably take the form of lateral flow assays. Especially preferred are such assays which are lateral flow immunochromatographic assays employing two coloured particle labels as discussed above. In constructing a test strip or sheet for such an assay, to preserve the universality of the detection zone, the test strip or sheet providing the detection zone may preferably be joined in liquid flow contact with a separate label release zone [15] which is capable of releasing into liquid drawn into that zone the required labelled reagents [2, 3], e.g. two labelled antibodies or labelled antibody and labelled analyte. The label release zone may, for example, be a glass fibre pad impregnated with the required labelled reagents.

The test strip or sheet [16] providing the detection zone will preferably comprise nitrocellulose. For example, for this purpose nitrocellulose sheet may be laminated onto a backing support [17], e.g. plastic sheet. The test strip or sheet providing the detection zone may be nitrocellulose card. The specific binding partner [11] to be immobilised to form the detection zone [1] may be applied to the nitrocellulose by known techniques for immobilising reagents for lateral flow assays such as by applying a solution of the reagent using an Isoflow™ reagent dispenser (Imagene, USA) or by employing an ink-jet dispenser. Two or more specific binding reagents suitable for provision of a universal detection zone may each be immobilised in separate zones on a test strip or sheet thereby enabling multiple assays as discussed above to be carried out simultaneously for different analytes in a single test sample. Following provision of the detection zone(s), non-detection zone regions of the supporting strip or sheet may be blocked in conventional manner, e.g. by treatment with a protein such as bovine serum albumin.

A test strip or sheet for use in a lateral flow method of the invention may also comprise a sample receiving member or pad [18] proximal to the label release zone [15]. Such a sample receiving member or pad may be made of any bibulous material capable of absorbing liquid rapidly. Distal to the detection zone in the direction of intended liquid flow [19], a test strip or sheet of the invention may further comprise an absorbent wicking pad [20].

Methods of constructing such test strips and sheets are well known. For further details of possible construction methods, reference may be made for example to European Patent no 0291194 already referred to above.

A test strip or sheet for a lateral flow assay of the invention may be inserted into a housing, e.g. a plastic housing, providing a window or windows over the detection zone (s). The invention also extends to lateral flow devices incorporating a test strip or sheet for carrying out a method of the invention.

Other Liquid Flow Devices

It will be appreciated that a test strip or sheet presenting a universal detection zone as discussed above may also be incorporated into a flow through device of conventional form. In this case, the liquid sample and required labelled reagents for performing an assay of the invention will be simply applied to the test strip or sheet, optionally via a filtering means.

Kits

As indicated above, kits comprising (i) a test strip or sheet providing a combined analyte detection and control zone in accordance with the invention and (ii) two labelled reagents carrying distinguishable labels, one of which will bind to the analyte detection/control zone regardless of the presence of target analyte, constitute a further aspect of the invention.

The two labelled reagents may be mixed together or kept separate. By "labelled" in this context will be understood as directly labelled or provided together with a secondary labelling reagent, e.g. secondary labelled antibodies. A secondary labelling reagent may also be separate from other kit reagents.

A kit of the invention may comprise a test strip or sheet as described above for carrying out a lateral flow assay. A kit of the invention may comprise other components. For example, where the test sample is to be collected from a test subject, the kit may comprise a fluid collection means, e.g. an oral fluid collection device or swab or a vessel such as a vessel suitable for collection of a urine or blood sample. A kit for use in carrying out a lateral flow method of the invention may include a portable reading device into which a housing as described above may be fitted for immobilised label detection in the detection zone(s), e.g. a reader providing an automatic read-out of colour in the detection zone (s). Such kits are applicable to both assays of the invention employing a universal analyte detection/control zone [11] and assays of the invention employing a mixture of two immobilised reagents in an analyte detection/control zone [12] as will now also be described in more detail.

The Mixed Capture Zone Embodiment

Assays of this embodiment rely on a specific binding reaction in the analyte detection zone/capture zone which is independent of the specific complexing of reagents with target analyte. As indicated above, for this purpose, the capture zone will present immobilised capture reagent [21] for the specific binding assay for target analyte [13], e.g. immobilised analyte-protein conjugate for a competitive binding assay or immobilised anti-analyte antibody for a competitive assay or a sandwich assay and, interdispersed therewith, a second immobilised reagent [22] to bind a labelled reagent (the control reagent) [4] independently of target analyte. Preferably, the control labelled reagent will be of the same molecular class as the labelled reagent for analyte detection so that both labelled reagents have substantially the same migration characteristics in performance of the method. Thus, for example where a labelled IgG antibody is used for complexing with target analyte, the control reagent will also desirably be a labelled IgG antibody, e.g. a labelled antibody specific for an immobilised antibody.

The labels may again be selected as above. Thus, they may be selected from any of the conventional types of labels used in specific binding assays, but will preferably be selected from labels providing a direct visual signal. Preferably, the chosen labels will be coloured labels of visually distinguishable contrasting colours whereby immobilisation of both labels is indicated by a colour combination. Such labels may be coloured particles such as coloured latex beads or colloidal gold. Thus, for example, where the specific binding assay for target analyte is chosen to be of a sandwich immunoassay format employing immobilised anti-analyte antibody, one labelled reagent may be a second anti-analyte antibody carrying coloured latex beads of one colour and the second labelled reagent (the control reagent) will then desirably be labelled antibody which binds a different unrelated antigen immobilised in the capture zone and carries coloured latex beads of a different colour. In this case, a negative sample not containing target analyte will be indicated by the colour of the capture zone being the colour of the control reagent label. With increasing analyte, the colour of the detection zone will be seen as a combination of the colours of the immobilised labels (see Example 3). Thus, by employing two coloured labels and a mixed reagent capture zone as discussed above a quantitative or semi-quantitative assay is again enabled by observing the precise colouring of the detection zone.

Instead of immobilised anti-analyte antibody, the mixed reagent capture zone may include immobilised analyte for a competitive immunoassay. In this case, again there will be employed two labelled antibodies with detectably distinguishable colour labels, labelled anti-analyte antibody and a labelled control antibody.

It is emphasised once again that all methods of the invention employing a competitive assay format for target analyte detection have the advantage over conventional liquid flow assays employing a competitive specific binding assay format that positive samples equate with a positive label signal.

Samples

Liquid samples to be used in a method of the invention may consist of, or be derived from, both biological and environmental samples. They may be, for example, urine samples, serum samples derived from blood, or oral fluid or buffer-diluted oral fluid samples. A suitable sample may be derived from an environmental source or swab.

Applications

Methods of the invention have wide applicability in the clinical field for laboratory, point-of-care and on-site testing. They may for example be used in diagnosis of infectious disease, e.g. detection of a viral infection such as infection with hepatitis B, hepatatis C or HIV. In this case, diagnosis of an infectious disease may simply be equated with detection of one colour and negative samples will be clearly shown by detection of a different colour in a test strip or sheet detection zone. Methods of the invention may also find much use in hormone testing, e.g. detection of hCG for pregnancy testing. Methods of the invention are also applicable to drug testing in which case the target analyte may be a drug or drug metabolite. Many other applications will be immediately apparent to those skilled in specific binding assays.

The following examples illustrate both of the assay embodiments discussed above.

EXAMPLES

Example 1

Pregnancy Test Employing a Universal Capture Zone

The protocol requires an anti-beta hCG antibody labelled with colloidal gold and anti-alpha hCG antibody which is both biotinylated and conjugated to green latex particles. The antibody reagents can be mixed together or kept separate at an appropriate ratio. They can be used either in liquid or dry form.

A nitrocelluose membrane strip or sheet is provided having a combined analyte detection and control zone (the capture zone) in the form of a dot or line coated with avidin, streptavidin or neutravidin. The nitrocelluose membrane may optionally be joined to a label release pad to which the labelled reagents are applied.

If a negative urine sample is mixed with the two labelled reagents and allowed to migrate up the nitrocellulose test membrane and over the capture zone only a green dot or line will appear as only the biotinylated antibody carrying the green latex particles will be captured. If a positive urine sample is mixed with the two labelled antibodies, the labelled antibody pair will form a complex with hCG and both colour labels will become immobilised in the capture zone of the test membrane which will be visualised as a red to brown colour. By controlling the intensity and ratio of each of the colour labels, the positive signal may be made red for hCG concentrations of interest indicative of a positive pregnancy test.

Example 2

Pregnancy Test Employing a Mixed Capture Zone

Again for this protocol an anti-beta hCG antibody is required which is labelled with colloidal gold. Also required is chicken IgY antibody (available from Alchemy Laboratories, Dundee) labelled with green latex particles. The labelled reagents may be mixed together or kept separate. They may be used in liquid or dry form.

A nitrocellulose test membrane is provided having a combined analyte detection and control zone formed by coating a dot or line region with a mixture of anti-alpha hCG antibody and anti-chicken IgY antibody in a single dispensing operation. This membrane may optionally be joined to a label release pad impregnated with the two labelled reagents.

If a negative urine sample is mixed with the two labelled reagents and is allowed to migrate up the nitrocellulose test membrane and over the capture zone, only a green dot or line will appear as the chicken antibody signal reagent is captured. If a positive urine sample is mixed with the two labelled reagents, they will both bind in the capture zone which will appear a red to brown colour. Again by controlling the intensity and ratio of each of the coloured particle labels, the positive signal may be made red for hCG concentrations of interest for a positive pregnancy test.

Example 3

Competitive Assay Employing a Universal Capture Zone

A biotinylated hapten, e.g. drug or drug metabolite, is labelled with blue latex beads and a corresponding anti-hapten antibody capable of binding the biotinylated hapten (raised to a hapten-protein conjugate) is provided labelled with yellow latex beads. A nitrocellulose membrane is provided with a capture zone coated with immobilised biotin specific binding protein, e.g. avidin, streptavidin or neutravidin. If a negative liquid sample without the hapten as labelled is mixed with the labelled reagents and allowed to migrate over the capture zone, the capture zone will be seen as a combination of blue and yellow colour, i.e. a shade of green, due to immobilisation of both labelled reagents. If a positive liquid sample is mixed with the two labelled reagents and allowed to migrate over the capture zone, the capture zone will become a blue colour due to capture of solely or mainly the biotinylated and colour particle-labelled hapten. The yellow particle-labelled antibody will complex with test sample hapten analyte.

Variations of all the above examples will be readily apparent to those skilled in carrying out specific binding assays.

The invention claimed is:

1. A liquid flow assay for detection of a target analyte in a liquid sample wherein the liquid sample flows through or along a test strip or sheet comprising a porous material and said test strip or sheet has a detection zone for said analyte wherein said analyte is detected by a specific binding assay of a sandwich or competitive format, characterised in that:
said detection zone is a single combined analyte detection and control zone wherein any target analyte is contacted with a first labelled reagent and a second labelled reagent provided as mobile reagents and carrying detectably distinguishable labels, and wherein both said first and second labelled reagents are components of the specific binding assay for target analyte, one of said labelled reagents additionally carrying a first member of a specific binding partner pair which binds to the second member of said pair immobilised in said detection zone, said immobilised second member of said specific binding partner pair not binding target analyte,
whereby irrespective of whether said sample is a positive or negative sample a captured label signal is detectable in the detection zone, positive and negative samples being distinguishable by detection of different captured label signals.

2. An assay as claimed in claim 1 wherein said first member of a specific binding partner pair is biotin and said detection zone presents an immobilised specific binding protein for biotin.

3. An assay as claimed in claim 1 wherein said first and second labelled reagents are both labelled antibodies which bind the target analyte and said specific binding assay is a sandwich immunoassay.

4. An assay as claimed in claim 1 wherein said labelled reagents are labelled with colour labels of visually contrasting colour whereby immobilisation of both labels in the detection zone is detected by detection of a colour combination.

5. An assay as claimed in claim 4 wherein said labels are selected from colloidal gold and coloured latex particles.

6. An assay as claimed in claim 1 wherein said specific binding assay is an immunoassay.

7. An assay as claimed in claim 1 which employs a flow through device.

8. An assay as claimed in claim 1 which is a lateral flow immunochromatographic assay.

9. An assay as claimed in claim 1 wherein said first labelled reagent is a labelled antibody which binds the target analyte and said second labelled reagent is labelled analyte or analyte analogue.

10. A kit for carrying out an assay as claimed in claim 1 which comprises (i) said first and second labelled reagents and (ii) a test strip or sheet comprising a porous material and providing said detection zone.

11. A test strip or sheet for performing a lateral flow assay according to claim 8 which has the following features:
(i) a test strip or sheet comprising a porous material which provides said detection zone; and
(ii) joined to, or integral to, said strip or sheet providing said detection zone, a label release zone which is capable of releasing into liquid drawn into that zone said first and second labelled reagents.

12. A test strip or sheet as claimed in claim 11 wherein said labelled reagents carry labels selected from colloidal gold and coloured latex particles.

13. A test strip or sheet as claimed in claim 11 inserted into a housing.

14. A lateral flow device incorporating a test strip or sheet according to claim 11.

* * * * *